United States Patent [19]

Koppel et al.

[11] 4,355,172

[45] Oct. 19, 1982

[54] PROCESS FOR 4-(D-3-AMINO-3-CARBOXYPROPOXY)-PHENYLGLYOXYLIC ACID OXIME DERIVATIVES

[75] Inventors: Gary A. Koppel; Robin D. G. Cooper, both of Indianapolis, Ind.

[73] Assignee: Eli Lilly and Company, Indianapolis, Ind.

[21] Appl. No.: 825,344

[22] Filed: Aug. 17, 1977

Related U.S. Application Data

[63] Continuation-in-part of Ser. No. 739,160, Nov. 5, 1976, abandoned.

[51] Int. Cl.$^3$ ............... C07C 125/065; C07C 125/067
[52] U.S. Cl. .................... 560/29; 260/239 A
[58] Field of Search ........................... 560/29

[56] References Cited

U.S. PATENT DOCUMENTS

| | | | |
|---|---|---|---|
| 3,852,290 | 12/1974 | Nagasawa et al. | 560/32 |
| 3,875,207 | 4/1975 | Iselin et al. | 560/29 |
| 3,891,692 | 6/1975 | Ueber et al. | 560/32 |
| 3,923,977 | 12/1975 | Aoki et al. | 260/239 A |
| 4,237,305 | 12/1980 | Kamiya et al. | 562/464 |

FOREIGN PATENT DOCUMENTS 830934 1/1976 Belgium ........................... 560/29

OTHER PUBLICATIONS

Lawson et al., J.A.C.S., 83, 1509 (1961).
Morrison & Boyd, "Organic Chem.", Allyn & Bacon, Inc., Boston, Mass., 3rd Ed., p. 674 (1973).
Lawson et al., J.A.C.S., 84, 1715–1718 (1962).
Mashimoto et al., J.A.C.S., 98(10), 3023–3025, 1976.
Wagner & Zook, Synthetic Organic Chem., John Wiley & Sons, Inc., pp. 565–573 & 585–589 (1965).
McOmie, Protective Groups in Organic Chem., Plenum Press, pp. 58, 59, 86, 87, 185–187, 210–211 (1973).
Bittner et al., Chem. Ind., (London) p. 281 (1975).

*Primary Examiner*—G. T. Breitenstein
*Attorney, Agent, or Firm*—William B. Scanlon; Arthur R. Whale

[57] ABSTRACT

Process for 4-(D-3-amino-3-carboxypropoxy)phenylglyoxylic acid oxime as an amino-protected ester comprising alkylating an amino-protected D-methionine silyl ester with an alkyl or benzyl iodide; cyclizing the alkylsulfonium iodide to an amino-protected D-homoserine lactone; hydrolyzing the lactone to an amino-protected D-homoserine in aqueous base; coupling, to form an ether, the amino-protected D-homoserine as an ester with an ester of 4-hydroxyphenylglyoxylic acid; and forming the oxime of the ether or alternatively coupling the D-homoserine ester with a protected-oxime of an esterified 4-hydroxyphenylglyoxylic acid. The product is useful in preparing the antibiotic FR 1923.

10 Claims, No Drawings

PROCESS FOR 4-(D-3-AMINO-3-CARBOXYPROPOXY)-PHENYL-GLYOXYLIC ACID OXIME DERIVATIVES

CROSS REFERENCE TO RELATED APPLICATION

This application is a continuation-in-part of co-pending application Ser. No. 739,160 filed Nov. 5, 1976, now abandoned.

BACKGROUND OF THE INVENTION

This invention relates to a process for preparing 4-(D-3-amino-3-carboxypropoxy)phenylglyoxylic acid oxime in the form of an amino-protected ester and to intermediates useful therein. In particular, this invention relates to a stereospecific synthesis of the 3-acyl side chain portion of the β-lactam antibiotic FR 1923. Antibiotic FR 1923, nocardicin, is represented by the following structural formula

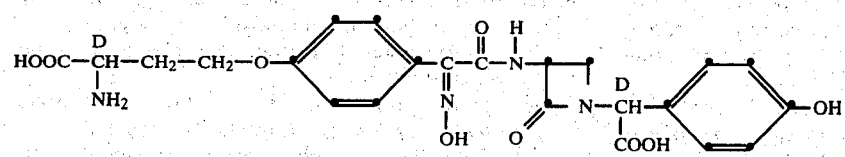

The antibiotic is described in Belgian Pat. No. 830934 and by H. Aoki et al., 15th *Interscience Conference on Antimicrobial Agents and Chemotherapy,* Abstract No. 97, September, 1975.

FR 1923 has previously been prepared by culturing *Nocardia uniformis* var. tsuyamanensis ATCC 21806 in aqueous nutrient media, isolating the antibiotic substance from the fermentation broth and purifying the isolate.

The product obtained in the process of this invention and certain derivatives thereof are useful in the total chemical synthesis of FR 1923 as described in co-pending application Ser. No. 739,161, filed Nov. 5, 1976, now U.S. Pat. No. 4,158,004. As disclosed therein, the nucleus of FR 1923, 1-(α-carboxy-4-hydroxybenzyl)-3-amino-2-azetidinone and preferably an ester thereof represented by the formula

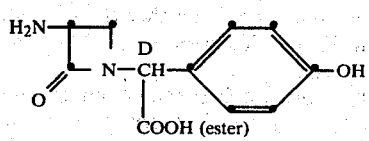

is acylated with an esterified and amino-protected active carboxylic acid derivative of 4-(D-3-amino-3-carboxypropoxy)-phenylglyoxylic acid oxime. After acylation, the ester groups are de-esterified and the amino-protecting group of the side chain is removed to provide the antibiotic FR 1923.

DETAILED DESCRIPTION

The process of this invention provides a stereospecific synthesis of an esterified and amino-protected 4-(3-amino-3-carboxypropoxy)phenylglyoxylic acid oxime represented by the following formula A

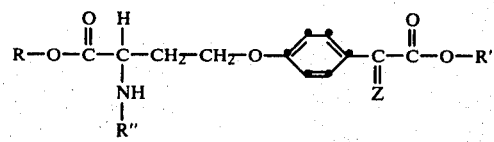

wherein R and R' independently represent hydrogen or a carboxylic acid blocking group; R" is hydrogen or an amino-blocking group; and wherein Z is =O or a group of the formula

=N-O-Z' wherein Z' is hydrogen, acetyl, chloroacetyl, p-methoxybenzyl or triphenylmethyl.

According to the process of this invention, an amino-protected trimethylsilyl ester of D-methionine is converted via a stereospecific synthesis to an amino-protected D-homoserine lactone and the D-lactone is reacted with base to provide the amino-protected D-homoserine. The free carboxylic acid group of the D-homoserine product is esterified and the amino-protected esterified D-homoserine is coupled via an etherification reaction with an ester of 4-hydroxyphenylglyoxylic acid or a protected oxime thereof to afford the amino-protected diester of 4-(D-3-amino-3-carboxypropoxy)phenylglyoxylic acid or the protected oxime derivative thereof. The ester group of the phenylglyoxylic or oxime derivative moiety of the product is deesterified to provide the free keto acid or protected oxime thereof. The free keto acid can be reacted with hydroxylamine to provide the oxime derivative.

In the process of this invention, D-homoserine or an amino-protected derivative thereof is first synthesized via a stereospecific synthesis employing D-methionine. According to this step in the overall process, an amino-protected methionine as the free acid or as a salt represented by the formula 1 in the following reaction scheme is converted in situ in an inert solvent to a trimethylsilyl ester derivative and the ester is reacted at a temperature between about −15° and about 40° C. with a $C_1$–$C_4$ alkyl iodide or with benzyl iodide to form the alkylated methionine derivative, an alkyl or benzylsulfonium iodide represented by the formula 2. The sulfonium iodide in the form of the silyl ester is reacted in an inert solvent with an alkali metal $C_1$–$C_4$ alkoxide to provide the amino-protected D-homoserine lactone represented by the formula 3.

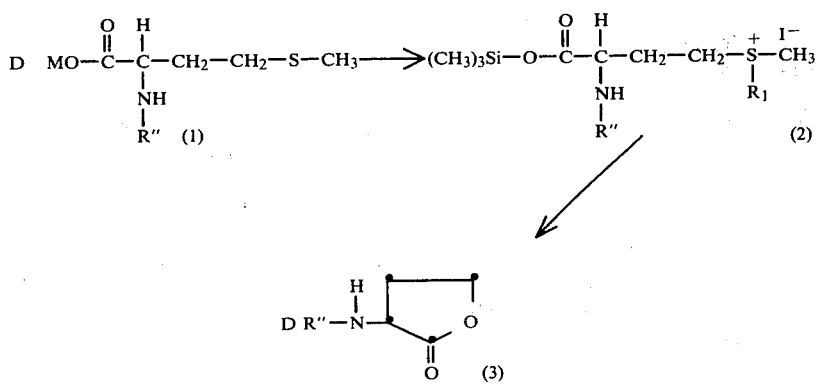

(1) (2) (3)

In the above reaction scheme, R" represents an amino-protecting group, M represents the cation of the salt formed with an alkali metal base or with an organic primary or secondary amine, and $R_1$ is $C_1$–$C_4$ alkyl or benzyl.

Amino-blocking groups represented by R" which are suitable in the present process include t-butyloxycarbonyl, benzyloxycarbonyl, p-nitrobenzyloxycarbonyl, 2,2,2-trichloroethoxycarbonyl, cyclopentyloxycarbonyl, and like protecting groups. A preferred protecting group of this invention is the t-butyloxycarbonyl group (t-BOC).

M in the above formula 1 represents hydrogen or the cation of a salt formed with the alkali metal hydroxides and carbonates such as sodium hydroxide, sodium carbonate, potassium hydroxide, potassium carbonate, and lithium carbonate. M also represents the cation of the salts formed with an organic amine such as the $C_1$–$C_4$ alkyl, cycloalkyl, and aralkyl primary amines, for example, methylamine, isopropylamine, n-butylamine, cyclohexylamine, and benzylamine; the lower alkyl, cycloalkyl, and aralkyl secondary amines, for example, dimethylamine, di-n-butylamine, di-cyclohexylamine, dibenzylamine, and like amines. A preferred amine salt of the amino-protected methionine starting material in this invention is the salt formed with dicyclohexylamine.

The alkyl iodides which can be employed in the preparation of the alkylsulfonium iodide derivatives of methionine are exemplified by methyl iodide, ethyl iodide, isopropyl iodide, and n-butyl iodide. Methyl iodide is a preferred alkylating agent.

The formation of the trimethylsilyl ester of the amino-protected methionine or with the salt form thereof is carried out prior to the alkylation reaction to block the carboxylic acid group during the alkylation. Trimethylsilylating agents which can be employed in preparing the silyl ester include, for example, trimethylsilyl chloride, mono-trimethylsilylacetamide (MSA), bis-trimethylsilylacetamide (BSA) and hexamethyldisilazane. Trimethylsilyl chloride is used to form the silyl ester when M in the above formula 1 is the cation of the salt form. MSA, BSA and hexamethyldisilazane are used to form the ester when M is hydrogen.

Solvents which are suitable in the above reaction include the common organic aprotic solvents such as tetrahydrofuran, dioxane, the dimethyl ether of ethylene glycol, acetonitrile, propionitrile, dimethylformamide, dimethylacetamide and like solvents.

The alkylsulfonium iodide represented by the above formula 2 is reacted in an inert aprotic solvent at a temperature between about 25° C. and about 80° C. with an alkali metal $C_1$–$C_4$ alkoxide to provide the amino-protected D-homoserine lactone represented by the above formula 3.

Solvents which are suitable in the formation of the lactone include for example tetrahydrofuran, the dimethyl ether of ethylene glycol, or dioxane. Alkali metal alkoxides useful in the process are exemplified by sodium methoxide, sodium ethoxide, potassium isopropoxide, and potassium t-butoxide. A preferred alkoxide is potassium t-butoxide.

Next in the process of this invention, the lactone represented by the above formula 3 is reacted in an aqueous solvent at a temperature between about −10° C. and about 25° C. with an alkali metal hydroxide to form, via hydrolysis of the lactone ring, the alkali metal salt of the amino protected D-homoserine represented by the following formula 4.

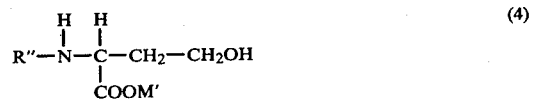

(4)

In the above formula 4, R" has the same meanings as herein above defined and M' represents a sodium or potassium cation.

The hydrolysis of the lactone is carried out by adding a solution of sodium or potassium hydroxide at a concentration of about 0.05 N to about 0.2 N to a cold solution of the amino-protected lactone in a water-miscible solvent maintained at a temperature between about −10° C. and about 5° C. Solvents such as dioxane, tetrahydrofuran, dimethylformamide and dimethylacetamide are suitable water-miscible solvents. The addition of excess base, i.e. greater than the stoichiometric amount, is to be avoided since excess base tends to epimerize the D-form.

The reaction is preferably carried out in aqueous dioxane and sodium hydroxide is the preferred alkali metal hydroxide.

After the addition of the base is complete, the reaction is allowed to warm to room temperature with stirring and is maintained at about that temperature until the reaction is complete.

The amino-protected D-homoserine salt is then esterified to block the carboxylic acid group and the amino-protected ester is coupled with an esterified 4-hydroxyphenylgyloxylic acid or an o-protected oxime thereof to form the amino-protected diester of 4-(D-3-amino-3-carboxypropoxy)phenylglyoxylic acid or the o- protected oxime represented by the formula 5 in the following reaction scheme.

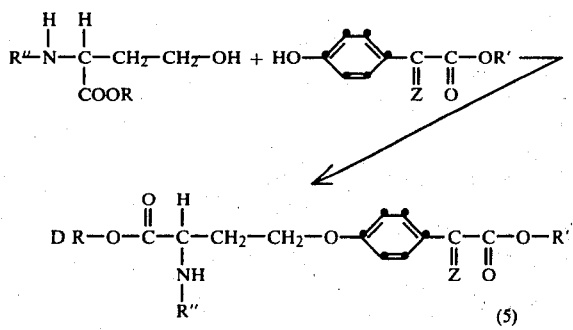

In the above reaction scheme, Z, R, R', and R" have the same meanings as defined previously.

The etherification reaction is carried out by reacting in an inert aprotic solvent the 4-hydroxyphenylglyoxylic acid ester or the protected-oxime derivative thereof with an equivalent amount of diethyl azodicarboxylate, adding to the reaction mixture an equimolar amount of the amino-protected D-homoserine ester followed by an equimolar amount of a tri-lower alkyl or triphenylphosphine. The reagents and reactants are preferably mixed at a temperature between about $-5°$ and $10°$ C. and after addition is complete the reaction mixture is stirred at about room temperature until the reaction is complete.

The reaction can be carried out in an aprotic solvent such as tetrahydrofuran, dioxane, the dimethyl ether of ethylene glycol, or other suitable solvent. Tetrahydrofuran is a preferred solvent.

Tri-lower alkylphosphines and tri-phenylphosphines which can be used in the above coupling (etherification) reaction are represented by the following structural formula.

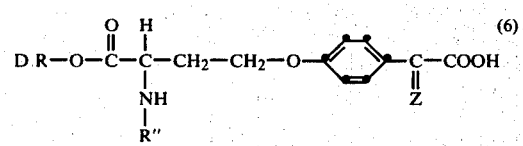

wherein $R_2$, $R_3$, and $R_4$ independently are $C_1$-$C_4$ alkyl, phenyl, or phenyl substituted with methyl or halogen. Examples of phosphines which can be employed in the coupling reaction include the trialkyl phosphines such as trimethyl phosphine, triethyl phosphine, tri-n-propyl phosphine, the trialkyl phosphines containing mixed alkyl groups, for example, dimethyl ether phosphine, diethyl methyl phosphine, and the phenyl and substituted phenyl phosphines, such as triphenyl phosphine, tri-(p-tolyl)phosphine, and tri-(p-chlorophenyl)-phosphine. A preferred phosphie for use with diethyl azodicarboxylate in the coupling reaction is triphenyl phosphine.

The product of the coupling reaction, the amino-protected diester represented by the formula 5 is selectively deesterified to remove only the carboxylic acid protecting ester group of the phenylglyoxylic acid moiety to provide the amino-protected monoester or a sodium or potassium salt thereof represented by the formula 6.

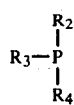

wherein R, R" and Z have the same meanings as previously defined.

The selective deesterification of compound 5 is made possible in the process of this invention by the proper choice of ester groups represented by the terms R and R'. According to the process of this invention, the ester group represented by the term R' is capable of being removed under conditions which leave the other ester group represented by the term R, the amino-protecting group R" and the oxime hydroxy protecting group Z' intact. As was previously mentioned, the product of the process of this invention is employed in the acylation of the nucleus of antibiotic FR 1923 as illustrated by the following reaction scheme.

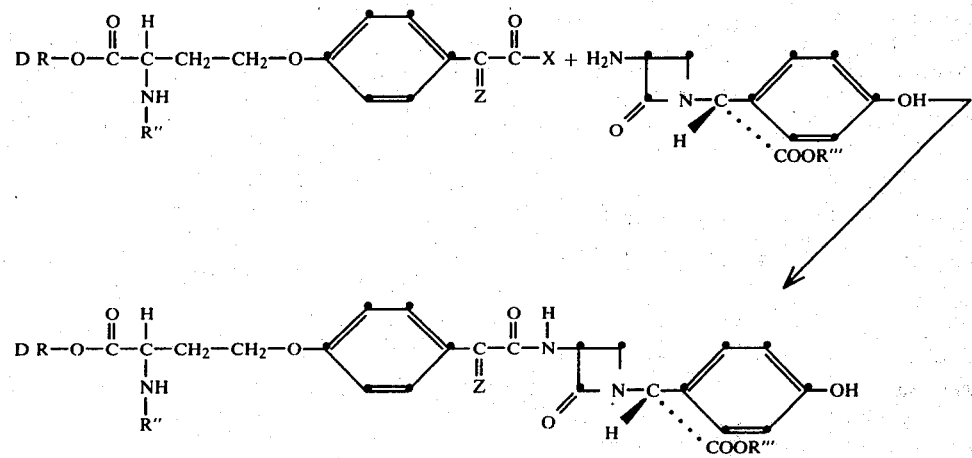

In the above reaction scheme R, R', R" and Z have the same meanings as defined previously; R'" is an ester forming group and X represents the carboxylic acid group activating moiety for acylation.

The selective deesterification of the ester group represented by R' renders only the desired carboxylic acid function available for acylation of the nucleus of FR 1923.

A number of carboxylic acid protecting groups are recognized in the art and from these may be chosen R ester groups and R' ester groups which are removed under different conditions so that the desired selectivity can be achieved. For example, the R ester group may be selected from among those known ester groups which are cleaved under acidic conditions, while the R' ester groups are chosen from those which are removable under reduction conditions. For example, R can represent diphenylmethyl, benzyl, 4-methoxybenzyl, 2,4,6-trimethylbenzyl, and phthalimidomethyl; carboxylic acid protecting groups which are removed under acid conditions. For example, diphenylmethyl (benzhydryl) esters can be deesterified with hydrogen chloride or hydrogen bromide in nitromethane or with trifluoroacetic acid at 0° C. Benzyl esters can be deesterified with hydrogen bromide and acetic acid. 4-Methoxybenzyl esters can be deesterified with trifluoroacetic acid at 0° C. 2,4,6-Trimethylbenzyl esters can be removed with trifluoroacetic acid or with hydrogen bromide and acetic acid. The phthalimidomethyl esters of carboxylic acids are removed with acids such as hydrogen chloride in ethyl acetate or dioxane, or with hydrobromic acid in acetic acid. Among the R' ester-forming groups which can be employed are p-nitrobenzyl, 2,2,2-trichloroethyl and phenacyl groups. These groups are examples of those which may be removed under reductive conditions, for example, with zinc in acetic acid or via electrolysis at the mercury cathode. In addition the p-nitrobenzyl and phenacyl ester groups can be selectively cleaved with sodium sulfide or sodium thiophenoxide.

The preferred R ester group of this invention is the diphenylmethyl group, while the preferred R' ester group of this invention is the p-nitrobenzyl group. The preferred oxime hydroxy protecting group is the p-methoxybenzyl group.

In the total synthesis of the antibiotic FR 1923 as disclosed in co-pending application Ser. No. 739,161, filed Nov. 5, 1976, the acylation of the FR 1923 nucleus can be carried out with either the mono-esterified-4-substituted-phenylglyoxylic acid (6) (the deesterification product of compound 5 above) wherein Z is

or with the oxime derivative thereof wherein Z is

Accordingly, when it is desired to employ the α-keto acid (formula 6, Z is =O) the diester (formula 5, Z is =O) is deesterified to provide the α-keto acid which is then converted to an active derivative for acylation of the FR 1923 nucleus. Alternatively, the α-keto acid can be reacted in an inert solvent with hydroxylamine hydrochloride in the presence of a hydrogen halide acceptor such as sodium bicarbonate to provide the α-hydroximino acid. Although the α-hydroximino carboxylic acid can be converted to an active derivative for use in acylation of the FR 1923 nucleus, it is preferable to protect the hydroximino group prior to acylation.

The O-acetyl oxime and O-chloroacetyl oxime are prepared by acylating the oxime of the α-keto acid with acetyl chloride or chloroacetyl chloride in an inert aprotic solvent in the presence of an acid-binding agent, for example, triethylamine. The o-trityl(triphenylmethyl) oxime is prepared by reacting the oxime with trityl chloride(triphenylmethyl chloride) in the presence of a hydrogen chloride acceptor such as pyridine. The o-(p-methoxybenzyl)oxime is prepared by reacting the oxime (formula 5, Z is =N-OH) with p-methoxybenzyl bromide and potassium t-butoxide.

The formation of the oxime group can be carried out early in the process, for example by preparing the oxime derivative of an ester of 4-hydroxyphenylglyoxylic acid, prior to the coupling reaction with the amino-protected ester of D-homoserine. The oxime when thus prepared is protected with one of the above described protecting groups to insure stability of the group during the remainder of the process. Likewise, the oxime group can be formed and then protected with the coupled phenylglyoxylic acid ester (formula 5, Z is =O) or alternatively the oxime can be formed following acylation of the nocardicin nucleus with the α-keto acid (formula 5, Z is =O).

In a preferred embodiment of the process of this invention, the dicyclohexylamine salt of N-t-butyloxycarbonyl D-methionine is treated in acetonitrile with trimethylsilyl chloride to provide in solution with trimethylsilyl ester. The silyl ester of the amino-protected methionine is converted to the methyl sulfonium iodide with methyl iodide and the sulfonium iodide reacted in tetrahydrofuran with potassium t-butoxide to provide N-t-butyloxycarbonyl D-homoserine lactone. The lactone is reacted in dioxane at about 0° C. with an aqueous solution of sodium hydroxide to effect hydrolysis of the lactone to yield N-t-butyloxycarbonyl D-homoserine sodium salt. The t-BOC protected D-homoserine salt is esterified to the diphenylmethyl ester with diphenylmethyl bromide and the product is coupled with p-nitrobenzyl 4-hydroxyphenylglyoxylate on reaction with diethyl azodicarboxylate and triphenylphosphine. The product, p-nitrobenzyl 4-[3-(t-butyloxycarbamido)-3-(diphenylmethoxycarbonyl)-propoxy]phenylglyoxylate, is reacted with sodium sulfide at 0° C. to effect the deesterification of the p-nitrobenzyl ester group and provide sodium 4-[3-(t-butyloxycarbamido)-3-(diphenylmethoxycarbonyl)propoxy]phenylglyoxylate. The deesterified product as the sodium salt is reacted in tetrahydrofuran with hydroxylamine hydrochloride in the presence of sodium bicarbonate to provide the oxime of the α-keto acid, 4-[3-D-(t-butyloxycarbamido)-3-(diphenylmethoxycarbonyl)propoxy]phenylglyoxylic acid oxime.

Another preferred embodiment of this invention comprises forming a protected-oxime derivative of an ester of 4-hydroxyphenylglyoxylic acid and thereafter coupling the protected-oxime ester with the amino-protected D-homoserine ester as described previously. The R' ester of the product is then selectively deesterified in the presence of the R ester group, the R'' amino-protecting group and the Z' oxime protecting group to provide the free carboxylic acid group for acylation.

In a specific example of this preferred embodiment, p-nitrobenzyl 4-hydroxyphenylglyoxylic acid is reacted at a temperature of about 140° C. with excess hydroxylamine hydrochloride in N,O-bis-trimethylsilyl trifluoroacetamide to form the oxime. The oxime ester is reacted with p-methoxybenzyl bromide and potassium t-butoxide in dimethylacetamide to form the protected-oxime ester, p-nitrobenzyl 4-hydroxyphenylglyoxylate O-(p-methoxybenzyl)oxime. The protected-oxime ester is then coupled with D-3-(diphenylmethoxycarbonyl)-3-(t-butyloxycarbamido)propanol using triphenylphosphine and diethylazodicarboxylate to provide the fully protected nocardicin side-chain, p-nitrobenzyl D-4-[3-(diphenylmethoxycarbonyl)-3-(t-butyloxycarbamido)-propoxy]-phenylglyoxylate O-(p-methoxybenzyl)oxime. The p-nitrobenzyl ester group of the coupling reaction product is selectively deesterified with sodium sulfide at 0° C. in aqueous tetrahydrofuran or alternatively by electrolytic reduction at the mercury cathode. The electrolysis is best carried out in dimethylformamide containing acetic acid as a proton source (catholyte solution) in an electrolysis cell comprising a mercury cathode (pool or ring), a platinum anode (gauze or wire) and an anolyte solution which is the same as the catholyte minus the substrate ester. The reduction potential (determined polarographically) is about −1.100 v. and the electrolysis is allowed to proceed at this potential until a sufficient number of coulombs has passed for a 4 electron reduction.

The above described specific example is illustrated by the following reaction scheme.

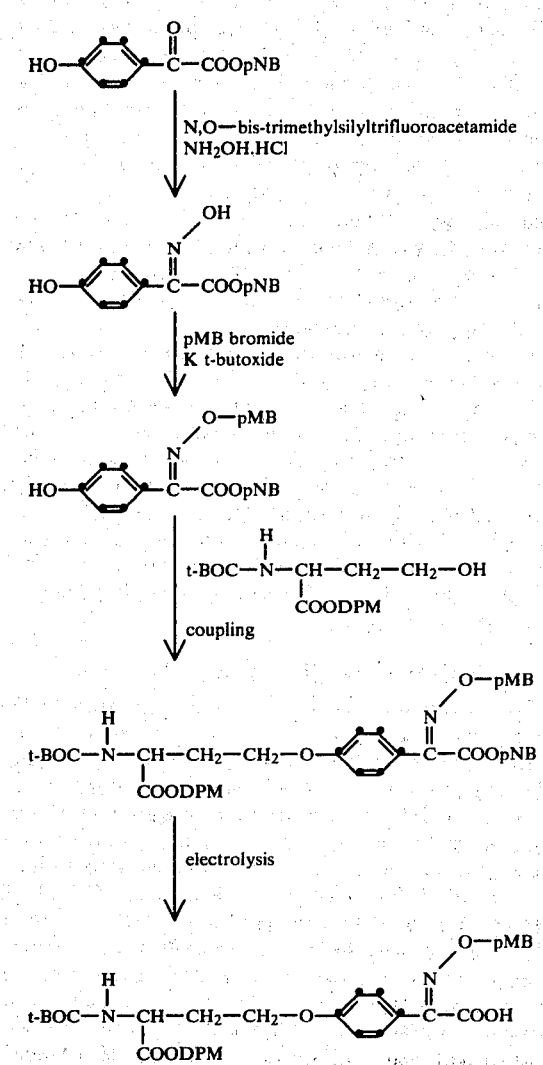

In the above reaction scheme t-BOC=t-butyloxycarbonyl; pNB=p-nitrobenzyl; pMB=p-methoxybenzyl; and DPM=diphenylmethyl.

The deesterified product is then used to acylate the nocardicin nucleus, for example with dicyclohexylcarbodiimide, and following acylation the t-butyloxycarbonyl amino-protecting group, the diphenylmethyl ester group and the p-methoxybenzyl oxime protecting group are all removed by treating the acylation product with trifluoroacetic acid in anisole.

As mentioned above, the compounds provided by the process of this invention are used to acylate the nucleus of antibiotic FR 1923. The acylation of the nucleus can be carried out by converting the α-keto acid or α-oximino acid (6) to an active carboxylic acid derivative such as an active ester, or azide or with the free acid in the presence of a condensing agent such as dicyclohexylcarbodiimide or diisopropylcarbodiimide.

A preferred method of acylation comprises the use of an active ester of the keto acid such as the active esters formed with 1-hydroxybenzotriazole(HBT) or N-hydroxysuccinimide.

Another preferred method of acylation of the nocardicin nucleus comprises coupling the protected-oxime acid, (formula 6, Z is =N-O-Z' wherein Z' is preferably p-methoxybenzyl) with a condensing agent for example, dicyclohexylcarbodiimide.

In one of its aspects, this invention relates to the novel amino-protected esters of 4-(D-3-amino-3-carboxypropoxy)phenylglyoxylic acid and the oxime and O-protected derivatives thereof which are represented by the foregoing formula A. Examples of the compounds represented are listed in the following Table wherein R, R', R", and Z have the same meanings as defined previously.

| R | R' | R" | Z |
|---|---|---|---|
| DPM[1] | pNB[2] | t-BOC[3] | =O |
| " | " | " | =N—OH |
| " | " | " | =N—O—C(=O)—CH₃ |
| " | phenacyl | " | =O |
| " | TCE[4] | " | =O |
| pMB[5] | pNB | " | =O |
| " | " | " | =N—OH |
| pMB | TCE | benzyloxycarbonyl | =O |
| " | " | " | =N—OH |
| DPM | pNB | cyclopentyloxy-carbonyl | =O |
| TMB[6] | pNB | t-BOC | =O |
| TMB | TCE | " | =N—OH |
| DPM | pNB | t-BOC | =N—O—pMB |
| p-MB | pNB | t-BOC | " |
| DPM | H | t-BOC | " |
| pMB | H | t-BOC | " |

[1]diphenylmethyl
[2]p-nitrobenzyl
[3]t-butyloxycarbonyl
[4]trichloroethyl
[5]p-methoxybenzyl
[6]2,4,6-trimethylbenzyl A preferred group of intermediates useful in the process is represented by the formula A when Z is =O (carbonyl).

A further preferred group is represented when Z is =O or =N-OH (oxime), R is diphenylmethyl, R' is p-nitrobenzyl and R" is t-butyloxycarbonyl.

An especially preferred group of intermediates of this invention is represented by the formula A wherein R is diphenylmethyl, R' is hydrogen or p-nitrobenzyl, R" is t-butyloxycarbonyl and Z is =N-O-p-methoxybenzyl [the O-(4-methoxybenzyl)oxime].

This invention is further exemplified by the following examples.

EXAMPLE 1

Preparation of N-t-butyloxycarbonyl D-methionine dicyclohexylamine salt

To a solution of 1040 g. (4 M) of 2,4,5-trichlorophenyl chloroformate in 1500 ml. of methylene chloride were added with stirring 296 g. (4 M) of t-butyl alcohol. The temperature of the solution dropped to about 5° C. on addition of the t-butyl alcohol and was warmed to about 25° C. with a warm water bath. Next, 516 g. (4 M) of quinoline were added dropwise over 6 hours to maintain the temperature at about 25° C. When addition was completed the reaction mixture was stirred for about 18 hours at room temperature. Thereafter, 1 liter of cold water was added to the mixture which was then filtered. The aqueous filtrate was extracted with methylene chloride and the extract was washed twice with 750 ml. portions of 1 N hydrochloric acid, twice with 500 ml. portions of water, twice with 750 ml. portions of 0.25 N sodium hydroxide, again with water and finally twice with 500 ml. portions of brine. The washed extract was then dried over magnesium sulfate and evaporated to dryness. The residue was dissolved in 3 l. of methyl alcohol with warming on a steam bath. The warmed methyl alcohol solution was diluted with 300 ml. of water by portionwise addition with stirring to precipitate the product as a crystalline solid. The mixture was refrigerated to induce further crystallization of the product. The product was collected by filtration and was washed on the filter with approximately 1600 ml. of methyl alcohol:water, 2:1, v:v, and was then dried at room temperature under vacuum. The dried product, t-butyl 2,4,5-trichlorophenyl carbonate, weighed 856 g. (72% yield) and melted at about 64°–66° C.

Elemental analysis: Theory: C, 44.40, H, 3.73, O, 16.13, Cl, 35.74: Found: C, 44.17, H, 3.86, O, 14.45, Cl, 36.06.

To a solution of 241.1 g. (0.810 M) of the above t-butylcarbonate ester and 109.6 g. (0.736 M) of D-methionine in 300 ml. of dioxane and 300 ml. of water were added 185.8 g. (1.84 M) of triethylamine. The solution was maintained at 50° C. for about 18 hours by means of a warm water bath. The solution was evaporated to obtain a residual oil and 800 ml. of ethyl acetate and 800 ml. of ethyl acetate and 800 ml. of water were added to the residue. The mixture was acidified with citric acid to pH 3.0 to 3.1 and the layers separated. The ethyl acetate layer was washed with 300 ml. of water and 300 ml. of brine. The washes were combined and washed with 300 ml. of ethyl acetate. The ethyl acetate layers were combined and were treated with 1100 ml. of 1 N potassium bicarbonate solution. The mixture was stirred until carbon dioxide evolution had ceased and the aqueous layer was separated from the ethyl acetate layer. The aqueous bicarbonate layer was washed twice with 300 ml. portions of ethyl acetate. Next, 1000 ml. of ethyl acetate were added to the aqueous layer which was acidified to pH 3.0 to 3.5 with citric acid. The ethyl acetate layer was separated and was washed three times with 300 ml. portions of water. The water washes were extracted with 300 ml. of ethyl acetate and the ethyl acetate wash and ethyl acetate layer were combined and dried over anhydrous sodium sulfate. The dried ethyl acetate solution was evaporated to dryness to yield an oily residue. The residue was dissolved in 700 ml. of ethyl acetate and the solution treated with decolorizing carbon on the steam bath. The mixture was filtered hot to remove the carbon and 1500 ml. of additional ethyl acetate were added to the filtrate.

With stirring 146 ml. of dicyclohexylamine were slowly added in portions to the ethyl acetate solution. The dicyclohexylamine salt of N-t-butyloxycarbonyl D-methionine began to crystallize during the addition of the amine. After addition of the amine was completed, approximately 400 ml. of petroleum ether were added to the crystallization mixture which was cooled in an ice bath for approximately 2 hours to complete crystallization. The product was filtered and washed on the filter with cold petroleum ether and was dried at 40° C. in a vacuum oven. The dried product weighed 199.5 g. (63% yield) and melted at about 136°–138° C. $[\alpha] = -12.8°$ (methyl alcohol).

EXAMPLE 2 p-Nitrobenzyl 4-hydroxyphenylglyoxylate

To a solution of 16.8 g. (0.1 mole) of 4-hydroxymandelic acid in 300 ml. of dimethylacetamide were added 11.2 g. of potassium t-butoxide with an additional 100 ml. of dimethylacetamide. The mixture was stirred at room temperature until a solution was obtained. p-Nitrobenzyl bromide (21.6 g., 0.1 mole) was added to the solution followed by 100 ml. of additional dimethylacetamide. The reaction mixture was stirred for 24 hours and was diluted with one liter of ethyl acetate. The mixture was washed repeatedly with water and dried over magnesium sulfate. The dried solution was evaporated to yield 25 g. (84 percent yield) of p-nitrobenzyl 4-hydroxymandelate.

The ester (4.25 g) was dissolved in 100 ml. of acetone and the solution was cooled to 0° C. With stirring, 10.6 ml. of Jones reagent were added dropwise. After addition was complete, the reaction mixture was stirred for 15 minutes and the reaction was then quenched by adding 3 ml. of isopropanol. The reaction mixture was extracted with 500 ml. of ethyl acetate and the extract was washed with an aqueous solution of sodium bicarbonate and dried. The extract was evaporated to yield 1.25 g. of p-nitrobenzyl 4-hydroxyphenylglyoxylate.

EXAMPLE 3 t-Butyloxycarbonyl D-Homoserine lactone

To a solution of 8.6 g. of N-t-butyloxycarbonyl D-methionine dicyclohexylamine salt in 250 ml. of acetonitrile were added 2.52 ml. of trimethylsilyl chloride. The solution was stirred at room temperature for 40 minutes and 100 ml. of methyl iodide were added. The reaction mixture was stirred at room temperature for 24 hours after which the mixture was evaporated to dryness in vacuo. The residue was dissolved in 400 ml. of tetrahydrofuran, 4.48 g. of potassium t-butoxide were added, and the solution was heated at the reflux temperature for 18 hours. The reaction mixture was allowed to cool and was evaporated to dryness under vacuum. The residue was dissolved in ethyl acetate and the solution washed with water, dilute aqueous sodium bicarbonate and 5% hydrochloric acid. The solution was dried over magnesium sulfate and evaporated to yield 2.7 g. (67% yield) of N-t-butyloxycarbonyl D-homoserine lactone $[\alpha]_{methanol} = +29°$ NMR (T60) CDCl₃: δ5.3 (1H, doublet, J=4, N-H), 4.0–4.6 (3H, multiplet) 2.2–3.0 (2H, multiplet, C₃-H) and 1.5 (9H, singlet t-BOC CH₃).

EXAMPLE 4

N-t-Butyloxycarbonyl D-homoserine sodium salt

A solution of 2.5 g. (12.4 mM) of N-t-butyloxycarbonyl D-homoserine lactone, prepared as described by Example 3, in 200 ml. of dioxane was cooled to 0° C. and 620 ml. of 0.02 molar sodium hydroxide were added over 30 minutes. After the addition of the base was complete the solution was allowed to warm to room temperature and was stirred for an additional 5 hours. The solution was concentrated under vacuum and the aqueous residue was washed with diethyl ether. The aqueous layer was lyophilized to yield 2.71 g. (91% yield) of N-t-butyloxycarbonyl D-homoserine sodium salt.

$[\alpha]_{water} + 13°$ (c=2)

NMR (T60) D₂O: δ3.5–4.0 (3H, multiplet), 2.6–3.0 (2H, multiplet) and 1.5 (9H, singlet).

EXAMPLE 5

N-t-Butyloxycarbonyl D-homoserine diphenylmethyl ester

To a solution of 0.610 g. of N-t-butyloxycarbonyl D-homoserine sodium salt in 10 ml. of hexamethylphosphoramide were added 0.626 g. of diphenylmethyl bromide. The solution was stirred at room temperature for 60 hours and 100 ml. of ethyl acetate were added. The organic layer was washed several times with water and was dried over magnesium sulfate. The dried solution was evaporated under vacuum to yield the esterified product as an impure oil. The product was purified via preparative thick layer chromatography (silica gel plates) using benzene-ethyl acetate, 7:3, v:v for elution. N-t-Butyloxycarbonyl D-homoserine diphenylmethyl ester was obtained in 64% yield (0.622 g.).

EXAMPLE 6

A solution of 0.487 g. (1.62 mM) of p-nitrobenzyl 4-hydroxyphenylglyoxylate in 25 ml. of tetrahydrofuran was cooled to 0° C. and a solution of 0.282 g. (0.62 mM) of diethyl azodicarboxylate in 10 ml. of tetrahydrofuran was added. Next, a solution of 0.622 g. of N-t-butyloxycarbonyl D-homoserine diphenylmethyl ester in 15 ml. of tetrahydrofuran was added followed by a solution of 0.425 g. (1.62 mM) of triphenylphosphine in 10 ml. of tetrahydrofuran. After the addition was complete, the reaction mixture was stirred at room temperature for 18 hours. The solvent was evaporated and the residue was chromatographed on silica gel thick layer plates using benzene-ethyl acetate, 6:1, v:v for elution of the purified product. The product, p-nitrobenzyl 4-[3-(t-butyloxycarbamido)-3-(diphenylmethoxycarbonyl)-propoxy]phenylglyoxylate represented by the following formula was obtained in 62% yield (683 mg.).

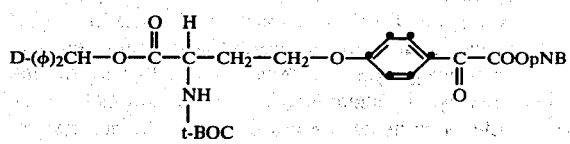

EXAMPLE 7

To a solution 339 mg. (0.495 mM) of the above phenylglyoxylate diester in 10 ml. of tetrahydrofuran and 1 ml. of water cooled to 0° C. were added 39 mg. of sodium sulfide. The mixture was warmed to room temperature with agitation until all of the sodium sulfide was in solution. The solution was cooled to 0° C. and was stirred in the cold for 30 minutes and at room temperature for 90 minutes. The reaction mixture was evaporated and the residue dissolved in ethyl acetate. Water was added and the pH adjusted to 2.5 with 5% hydrochloric acid. The organic layer was separated and washed with water and with a saturated solution of sodium bicarbonate. The organic layer was evaporated and the crude residue was triturated with chloroform-petroleum ether to yield 159 mg. (57% yield) of sodium 4-[3-(t-butyloxycarbamido)-3-(diphenylmethoxycarbonyl)propoxy]-phenylglyoxylate.

$[\alpha] = +9°$ (c=2 mg./ml. ethyl acetate)

NMR (T60) D₂O δ5.6 (1H, doublet, J=5 t-BOC N-H), 3.5–4.0 (2H, multiplet), 2.5–2.6 (2H, multiplet) and 1.5 (9H, singlet).

EXAMPLE 8

To a solution of 108 mg. of sodium 4-[3-(t-butyloxycarbamido)-3-(diphenylmethoxycarbonyl)propoxy]-phenylglyoxylate in 16 ml. of tetrahydrofuran were added 24 ml. of water, 0.276 g. of hydroxylamine hydrochloride, and next 0.336 g. of sodium bicarbonate. The reaction mixture was stirred at room temperature for one hour and again 0.276 g. of hydroxylamine hydrochloride and 0.336 g. of sodium bicarbonate were added. After stirring for 18 hours the same amounts of hydroxylamine hydrochloride and sodium bicarbonate were added and stirring was continued for 3 hours. Again the same amounts of hydroxylamine hydrochloride and sodium bicarbonate were added to the reaction mixture and the reaction mixture was stirred an additional 2.5 hours at room temperature. Ethyl acetate was added to the reaction mixture which was then acidified with 5% hydrochloric acid. The organic layer was separated and evaporated to yield 110 mg. of product which on drying weighed 90 mg. The nuclear magnetic resonance spectrum was in agreement with the following structural formula of the product:

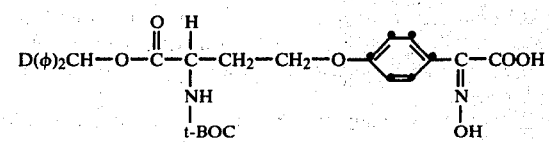

A thin layer chromatogram of the product run on a silica gel plate with chloroform:acetic acid, 4:1, v:v, showed one major spot for the product which gave a positive ferric chloride test.

$[\alpha] + 15$ (c=2, ethyl acetate).

NMR (T60) CDCl₃ δ4.5–5.0 (1H, multiplet), 4.4–3.7 (2H, multiplet), 2.7–2.0 (2H, multiplet) and 1.5 (9H, multiplet).

EXAMPLE 9 p-Nitrobenzyl p-hydroxyphenylglyoxylate oxime

To a mixture of 0.176 g. of p-nitrobenzyl p-hydroxyphenylglyoxylate and 1 g. of hydroxylamine hydrochloride were added 9 ml. of N,O-bis-trimethylsilyltrifluoroacetamide and the solution was stirred at a temperature of 140° C. for 2 hours. The reaction mixture was evaporated under reduced pressure and the residue was taken up in ethyl acetate. The ethyl acetate solution was washed with water and was then dried and evaporated. The oxime product was purified and isolated over silica gel preparative plates using toluene:ethyl acetate, 7:3, for elution. The product was located on the plate by means of UV light and the silica gel was scraped from the plate and the product extracted therefrom with ethyl acetate. The ethyl acetate was evaporated to yield 186 mg. of product. The product was crystallized from methylene chloride to yield 103 mg. of the crystalline material. The filtrate from the crystallization was diluted with petroleum ether to yield a second crop of 20 mg.

EXAMPLE 10 p-Nitrobenzyl p-hydroxyphenylglyoxylate O-(p-methoxybenzyl)-oxime

To a solution of 0.937 g. of the oxime, prepared as described in Example 9, in 50 ml. of dimethylacetamide was added 0.19 g. of potassium t-butoxide followed by a solution of 0.472 g. of p-methoxybenzyl bromide (80 percent pure) in 2 ml. of dimethyl acetamide. The resulting solution was stirred for 16 hours at room temperature and was then diluted with ethyl acetate. The whole was washed with water and with brine and was dried and evaporated. The reaction product mixture obtained as a residue was chromatographed over silica gel preparative plates by employing toluene:ethyl acetate, 7:3, to afford 0.269 g. of the O-(p-methoxybenzyl)-oxime product.

EXAMPLE 11

D-4-[3-(t-butyloxycarbamido)-3-(diphenylmethoxycarbonyl)-propoxy]phenylglyoxyic acid O-(4-methoxybenzyl)oxime To a solution of 40.6 mg. (0.105 mmole) of D-3-(t-butyloxycarbamido)-3-(diphenylmethoxycarbonyl)-propanol and 46 mg. (0.105 mmole) of the O-(p-methoxybenzyl)oxime, prepared as described in the preceding example, in about 20 ml. of dry tetrahydrofuran were added 27.6 mg. of triphenylphosphine and finally 218.3 mg. of diethyl azodicarboxylate. The reaction mixture was maintained under nitrogen and was stirred at room temperature for about 1 hour. The reaction mixture was then evaporated and the residue applied directly to silica gel preparative plates employing toluene:ethyl acetate, 7:3, for elution to afford 29 mg. of the title compound.

The nuclear magnetic resonance spectrum of the product showed the following signals:

NMR (T60) CDCl$_3$: 1.40 (s, t-butyl), 2.33 (t, —CH$_2$—), 3.78 (s, —O—CH$_3$), 3.95 (t, —CH$_2$—O—), 4.63 (t, —CH—), 5.20 (s, —O—CH$_2$), 5.33 (s, —O—CH$_2$—) and 6.50–8.33 (aromatic and amide) delta.

A solution of 250 mg. of the product, p-nitrobenzyl D-4-[3-(t-butyloxycarbamido)-3-(diphenylmethoxycarbonyl)propoxy]phenylglyoxylate O-(p-methoxybenzyl)oxime, in 40 ml. of reagent grade dimethylformamide containing 2 percent by volume of glacial acetic acid as a proton source aon 0.1 M tetraethylammonium perchlorate as an electrolyte was subjected to electrolysis at −1.100 v. The electrolysis cell was equipped with a saturated calomel electrode using a salt bridge containing 0.1 M tetraethylammonium perchlorate in a 1:1 misture of dimethylformamide:water. The working electrode (cathode) was a mercury ring having 14 cm$^2$ surface area. The auxiliary electrode (anode) was a platinum wire in an anolyte consisting of the catholyte solution without the substrate ester. The working and auxiliary electrodes were separated by a fine glass frit ring. The electrolysis was carried out until the total number of coulombs passed was sufficient for a four-electron transfer. The potential of the reduction (−1.100 v.) was predetermined in a polarogram.

The reduction product mixture was poured into ethyl acetate and the ethyl acetate solution was washed repeatedly with water. The solution was next washed with a saturated solution of sodium bicarbonate to form the sodium salt of D-4-[3-(diphenylmethoxycarbonyl)-3-(t-butyloxycarbamido)propoxy]phenylglyoxylic acid O-(p-methoxybenzyl)-oxime. The salt was soluble in the ethyl acetate and the solution was evaporated to dryness to yield the crude sodium salt as a dry residue. The sodium salt was leached with a mixture of chloroform and petroleum ether and was then redissolved in ethyl acetate. The solution of the salt was washed with 1 N hydrochloric acid, water, and then dried and evaporated to dryness to yield the title compound as the free acid.

We claim:
1. A process for preparing a compound of the formula

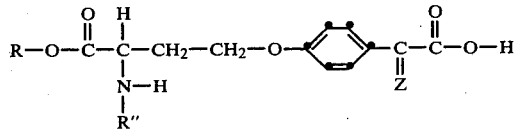

wherein
R is benzyl, 4-methoxybenzyl, 2,4,6-trimethylbenzyl, or diphenylmethyl;
R" is t-butyloxycarbonyl, 2,2,2-trichloroethoxycarbonyl, cyclopentyloxycarbonyl, benzyloxycarbonyl, or 4-nitrobenzyloxycarbonyl; and
Z is =O or a group of the formula

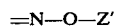

wherein Z' is hydrogen, acetyl, chloroacetyl, triphenylmethyl or p-methoxybenzyl; which comprises the steps of
(a) silylating an amino-protected D-methionine of the formula

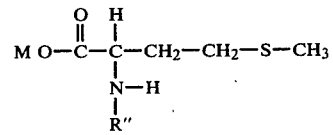

wherein M is hydrogen, an alkali metal cation or an ammonium cation derived from a primary or secondary C$_1$–C$_4$ alkyl, C$_5$ or C$_6$ cycloalkyl or benzyl amine, with a trimethylsilyl compound selected from the group of trimethylsilyl chloride, monotrimethylsilylacetamide, bistrimethylsilylacetamide, and hexamethyldisilazane to form the trimethylsilyl ester of the formula

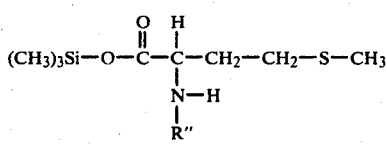

(b) alkylating said silyl ester with a $C_1$–$C_4$ alkyl iodide or benzyl iodide to form an alkylsulfonium iodide ester of the formula

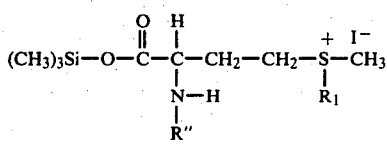

wherein $R_1$ is $C_1$–$C_4$ alkyl or benzyl;

(c) heating said alkylsulfonium or benzylsulfonium iodide ester in an inert aprotic solvent at a temperature between about 25° C. and about 80° C. with a $C_1$–$C_4$ alkali metal alkoxide to form an amino-protected homoserine lactone of the formula

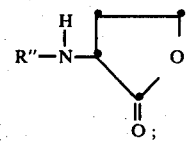

(d) hydrolyzing said lactone with an alkali metal hydroxide to form an amino-protected D-homoserine salt of the formula

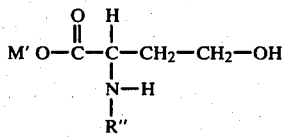

wherein M' is an alkali metal cation;

(e) esterifying said amino-protected homoserine to form an ester of the formula

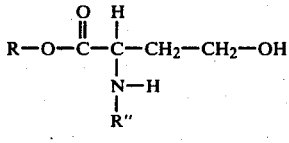

wherein R and R'' have the same meanings as defined above;

(f) reacting said ester in an inert aprotic solvent with a 4-hydroxyphenylglyoxylic acid ester of the formula

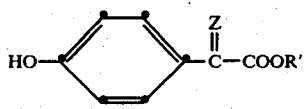

wherein R' is 4-nitrobenzyl, 2,2,2-trichloroethyl or phenacyl, an equimolar amount of diethyl azodicarboxylate and an equimolar amount of a phosphine of the formula

wherein $R_2$, $R_3$, and $R_4$ independently are $C_1$–$C_4$ alkyl, phenyl, or phenyl substituted with methyl or halogen, to form an amino-protected diester ether of the formula

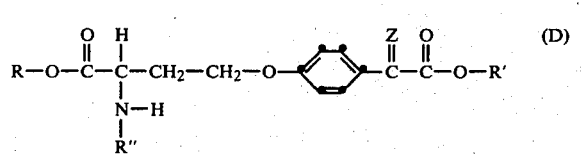

wherein R, R', R'' and Z have the same meanings as defined above; and (g) selectively de-esterifying said ether to form an α-keto or α-oximino acid of the formula

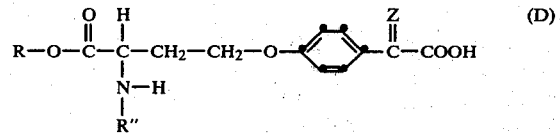

2. The process of claim 1 wherein Z is =O which comprises the further step of reacting said α-keto acid with hydroxylamine hydrochloride in the presence of an acid binding agent to form the α-ketoacid oxime.

3. The process of claim 1 wherein the alkyl or benzyl sulfonium iodide is heated with potassium t-butoxide.

4. The process of claim 1 wherein the phosphine is triphenylphosphine.

5. The process of claim 1 wherein M is the dicyclohexylammonium cation, R is diphenylmethyl and R' is p-nitrobenzyl.

6. The process of claim 1 wherein R'' is t-butyloxycarbonyl.

7. The process of claim 1 wherein the amino-protected methionine has the D-configuration.

8. The process of claim 1 wherein Z is a group of the formula

=N—O—Z'.

9. The process of claim 8 wherein R is diphenylmethyl, R' is 4-nitrobenzyl, R'' is t-butyloxycarbonyl and Z' is 4-methoxybenzyl.

10. The process of claim 8 wherein N-(t-butyloxycarbonyl)-D-homoserine lactone is hydrolyzed in dioxane with sodium hydroxide to form N-(t-butyloxycarbonyl)-D-homoserine; said D-homoserine is esterified with diphenyldiazomethane to form N-(t-butyloxycarbonyl)-D-homoserine diphenylmethyl ester; said ester is coupled with 4-nitrobenzyl 4-hydroxyphenylglyoxylate O-(4-methoxybenzyl)oxime with triphenylphosphine and diethylazodicarboxylate to form 4-nitrobenzyl 4-[D-3-(t-butyloxycarbamido)-3-(diphenylmethoxycarbonyl)-propoxy]phenylglyoxylate O-(4-methoxybenzyl)oxime; and said oxime is selectively de-esterified to form 4-[D-3-(t-butyloxycarbamido)-3-(diphenylmethoxycarbonyl)propoxy]phenylglyoxylic acid O-(4-methoxybenzyl)oxime.

* * * * *